(12) United States Patent
Bharara et al.

(10) Patent No.: US 7,505,867 B2
(45) Date of Patent: Mar. 17, 2009

(54) SYSTEM AND METHOD FOR PREDICTING MEDICAL CONDITION

(75) Inventors: Aavishkar Bharara, Rohini (IN); Joji George, Bangalore (IN); Ramkumar Saptharishi, Bangalore (IN)

(73) Assignee: General Electric Co., Schenectady, NY (US)

( * ) Notice: Subject to any disclaimer, the term of this patent is extended or adjusted under 35 U.S.C. 154(b) by 24 days.

(21) Appl. No.: 11/751,356

(22) Filed: May 21, 2007

(65) Prior Publication Data
US 2008/0294376 A1    Nov. 27, 2008

(51) Int. Cl.
*G06F 17/18* (2006.01)
*G06F 19/00* (2006.01)

(52) U.S. Cl. .................................. 702/181

(58) Field of Classification Search .......... 702/19, 702/179–181; 600/300, 483, 523
See application file for complete search history.

(56) References Cited

U.S. PATENT DOCUMENTS

| | | |
|---|---|---|
| 2004/0015337 A1 | 1/2004 | Thomas et al. |
| 2004/0219567 A1 | 11/2004 | Califano et al. |
| 2006/0036619 A1 | 2/2006 | Fuerst et al. |
| 2006/0136143 A1* | 6/2006 | Avinash et al. ............ 702/20 |
| 2006/0184489 A1* | 8/2006 | Weiner et al. ............ 706/46 |
| 2007/0294113 A1* | 12/2007 | Settimi ............ 705/3 |
| 2008/0046288 A1* | 2/2008 | Menon et al. ............ 705/3 |

* cited by examiner

*Primary Examiner*—Michael P Nghiem (57) ABSTRACT

In one embodiment, a method of deriving probability of a medical condition is provided. The method comprises obtaining a first medical data corresponding to a first medical subject from at least one medical information system, obtaining a second medical data corresponding to the first medical subject from an electronic data system, selecting at least one second medical subject with a second medical data substantially same as the second medical data of the first medical subject, obtaining medical condition data for the second medical subject, wherein the medical condition data includes data corresponding to a medical condition, correlating the first medical data with the medical condition data and deriving probability of the medical condition in the first medical subject based upon the first medical data and the medical condition data.

18 Claims, 6 Drawing Sheets

SYSTEM AND METHOD FOR PREDICTING MEDICAL CONDITION

FIELD OF INVENTION

The invention generally relates to system and method for deriving illness probability in a medical subject and more particularly to system and method for predicting probability of a medical condition in a medical subject.

BACKGROUND OF THE INVENTION

Picture Archival Communication Systems (PACS) is an industry term for the system and software that permits images from one or more imaging devices such as X-ray imaging device, Ultrasound imaging device, computed tomography device (CT), magnetic resonance imaging device (MRI) and Nuclear Medicine imaging device, to be electronically acquired, stored and transmitted for viewing or analysis. In addition, PACS acts like a central storage for a number of radiology documents such as images, reports, presentation states, videos, sound clips, other notes and alerting information. Multiple standards of communication such as Digital Imaging and Communication in Medicine (DICOM) and Integrating the Healthcare Enterprise (IHE) allow standardizing the export and communication of the radiology documents.

Authorized users can view the radiology documents, such as images of a medical subject, on diagnostic workstations. In addition to viewing the images, the users can also view data associated with the image such as name and sex of the medical subject. A radiologist and/or a physician typically use a diagnostic viewing application to view the data and images associated with the medical subject. A diagnosis performed by the radiologist and/or the physician on a medical condition possibly present in the medical subject is solely based on the information contained in the images and the data.

The radiologist and/or the physician may be unaware of additional information about the medical subject that may help in aiding the diagnosis in terms of providing a historical data of the medical subject.

Due to lack of this information, the radiologist and/or the physician may miss on opportunities to do accurate diagnosis. The diagnosis as in most cases is limited to manual inspection and may not be able to anticipate future problems. Hence the diagnosis may fail in providing a futuristic healthcare solution.

Hence there exists a need for a system and method of providing additional information associated with the medical subject thereby aiding the diagnosis.

BRIEF DESCRIPTION OF THE INVENTION

The above-mentioned shortcomings, disadvantages and problems are addressed herein which will be understood by reading and understanding the following specification.

In one embodiment, a method of deriving probability of a medical condition is provided. The method comprises obtaining a first medical data corresponding to a first medical subject from at least one medical information system, obtaining a second medical data corresponding to the first medical subject from an electronic data system, selecting at least one second medical subject with a second medical data based on the second medical data of the first medical subject, obtaining medical condition data for the second medical subject, the medical condition data being data corresponding to a medical condition of the second medical subject, correlating the first medical data with the medical condition data and deriving probability of the medical condition in the first medical subject based upon the first medical data and the medical condition data.

In another embodiment, an integrated information system is provided. The integrated information system comprises a data processing unit, at least one medical information system coupled to the data processing unit and an electronic data system coupled to the data processing unit. The medical information system is configured for providing a first medical data associated with a first medical subject. The electronic data system is configured for providing a second medical data associated with the first medical subject. The data processing unit is configured for deriving a probability of a medical condition in the first medical subject based on the first medical data and the second medical data.

In yet another embodiment, a computer program product stored in a computer readable media for predicting the probability of a medical condition in a first medical subject is provided. The computer program product comprises a routine for obtaining a first medical data corresponding to the first medical subject from at least one medical information system, a routine for obtaining a second medical data corresponding to the first medical subject from an electronic data system, a routine for selecting at least one second medical subject with a second medical data based on the second medical data of the first medical subject, a routine for obtaining medical condition data for the second medical subject, a routine for correlating the first medical data with the medical condition data and a routine for deriving probability of the medical condition in the first medical subject based upon the first medical data and the medical condition data.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The invention provides a system and method of providing additional information to a user, deriving probability of a medical condition in a medical subject. The user can be a medical staff such as a scientist, a clinician, a physician or a radiologist and the medical subject refers to an organism, a person or an animal. The medical condition can be defined as an abnormal condition or functioning of a part, organ, or system of the medical subject resulting from various causes, such as infection, genetic defect, or environmental stress, and characterized by an identifiable group of signs or symptoms. Thus, the system and method for predicting a medical condition in a medical subject include several components, each with its own function, but wherein their interaction results in an analysis tool for the user.

Figure 1:
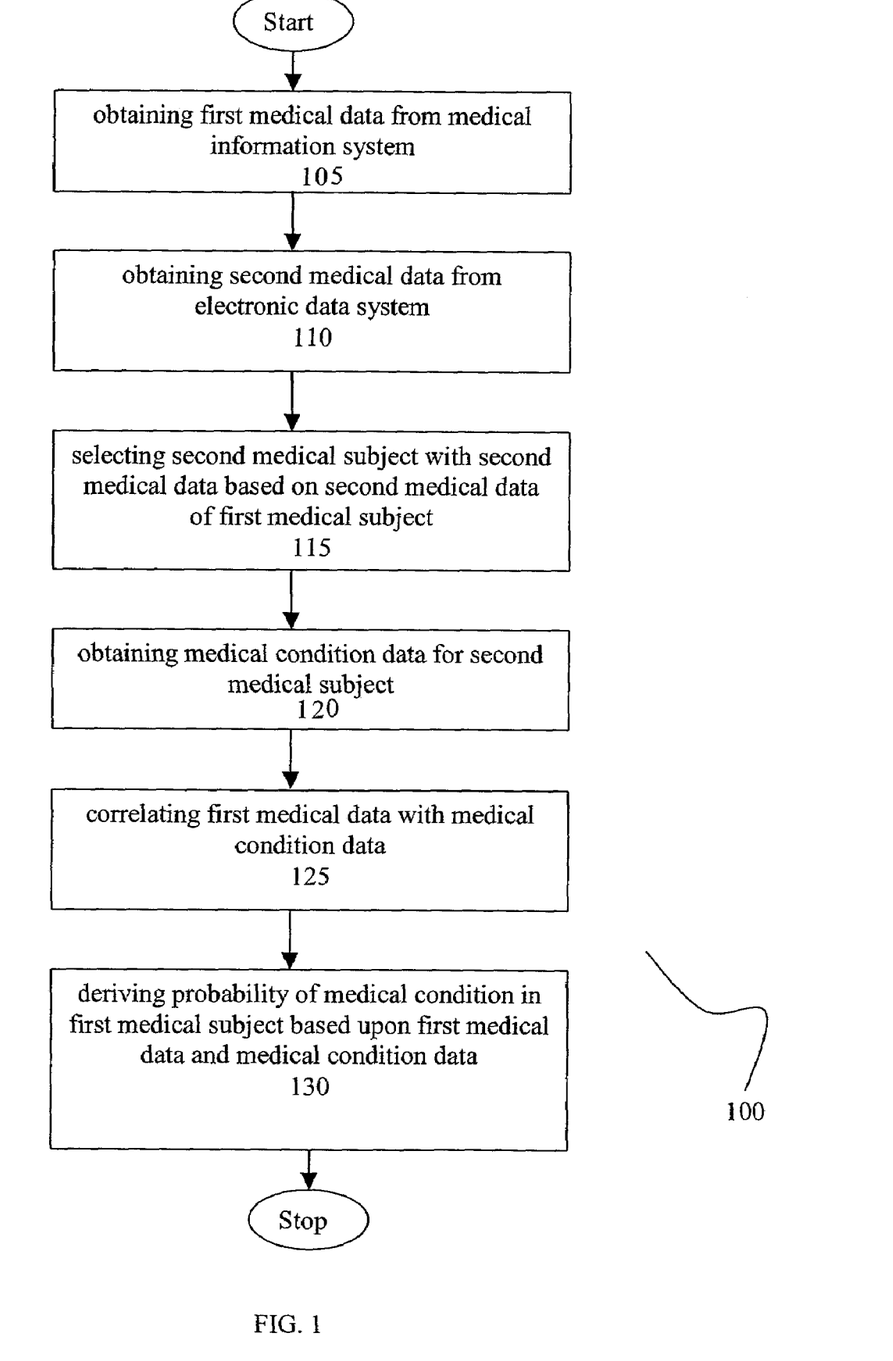
FIG. 1 shows a flow diagram of a method of predicting a medical condition in a medical subject in an embodiment of the invention.

FIG. 1 shows a flow diagram of a method 100 of predicting a medical condition in a first medical subject in one embodiment of the invention. The method 100 of predicting the medical condition includes obtaining or extracting a first medical data of the first medical subject from a medical information system step 105, obtaining or extracting a second medical data of the first medical subject from an electronic data system step 110, identifying at least one second medical subject with a second medical data based on the second medical data of the first medical subject step 115, obtaining medical condition data for the second medical subject step 120, the medical condition data comprising data regarding a medical condition of the second medical subject, comparing or correlating the first medical data with the medical condition data step 125 and outputting a resultant analysis that predicts the likelihood of occurrence of the medical condition in the first medical subject based on the patterns discovered in the medical condition data step 130.

The first medical data of a medical subject may include, diagnostic and demographic data of the medical subject. The diagnostic data may include images, reports, presentation states, videos, sound clips, other notes and alerting information. Further, the diagnostic data may include identification data of the medical subject, whereas the demographic data may include data provided by the medical subject, such as name, address, sex, phone numbers and so on. It is known that studying a single medical data such as the first medical data is insufficient for predicting the occurrence of a medical condition in the medical subject. Multiple indicators may be linked to the prediction of the medical condition. Thus, the users are expected to consider multiple variables or factors before accurately predicting the medical condition.

Numerous research findings have produced a great volume of data relating to such possible indicator factors that have been shown to be associated with the occurrence of the medical condition. For example, specific blood relations have been linked with the occurrence of certain genetically transmitted medical conditions. When the effects of certain factors are determined with respect to the occurrence of a medical condition, the users may more reliably predict the occurrence of the medical condition. This prediction is even more important when the medical subject indicates factors that may be linked to one another or their collective contribution to the occurrence of the medical condition can be identified.

Some of the examples of possible indicator factors include last name of the medical subject, ethnicity of the medical subject such as the region of residence of the medical subject, or ancestral data of the medical subject. The last name of the medical subject can be a good deciding factor in guiding the diagnosis of the medical subject. For instance, there may be a high probability of "Clintons" having a high blood pressure. Similarly, there may be a high probability of a medical subject staying in City X acquiring calcium calcification.

Further, a number of medical conditions may have gene based trending (aka genetic). Few of the genetically passed medical conditions may be passed through alternate generations. For instance, in a medical condition such as epilepsy, the probability of a third generation acquiring epilepsy is more if the first generation has recorded the presence of epilepsy albeit the second generation witnessing the absence of epilepsy. As an alternative consideration, the genes for causing epilepsy may still be present in the second generation but in a recessive form. In lieu of genetically passed medical conditions, the DNA of the medical subject can also be a deciding factor in identifying the occurrence of a medical condition in a medical subject and the probability of occurrence of the medical conditions in future. Thus, these indicator factors can be used as inputs for aiding in appropriate futuristic medical diagnosis.

Accordingly, it is desired to consider these indicator factors, collectively named as the second medical data in predicting the occurrence of a medical condition in a medical subject. As described in the above embodiments, the second medical data of a medical subject may include at least one of the last name of the medical subject, ethnicity of the medical subject, genetic data of the medical subject and ancestral, historical or hereditary data of the medical subject. Skilled artisans shall however appreciate that the examples of the second medical data mentioned above are not exclusive and the second medical data may include any data pertaining to the medical subject sans the diagnostic and demographic data.

For predicting the occurrence of a medical condition in the first medical subject, the first medical data of the first medical subject is to be viewed in the context of medical records of at least one other medical subject (a second medical subject) with a substantially same second medical data as that of the first medical subject. The medical record may be referred to as medical condition data of the second medical subject. The medical condition data is a data that can be collected over the course of diagnosis and treatments. In general, the medical condition data may include clinical, pathological, demographic, diagnostic, treatment and outcome data of the second medical subject. In addition, the medical condition data may include genetic medical data, medical history, physical handicaps, known medical conditions, known medical allergies, and current ailment conditions such as symptoms, duration, temperature, blood pressure, pulse rate, blood test data, urine test data, physician observations and the like. Additionally, the medical condition data may include drug data such as prescriptions, allergy information, drug interaction information, drug treatment information, overdose information and diagnostic data such as radiology information, laboratory information, clinical information, computed tomography (CT) images, ultra sound images, magnetic resonance images, X-ray images, laboratory test results, doctor progress notes, details about medical procedures, radiological reports, other specialist reports and demographic information.

Figure 3:
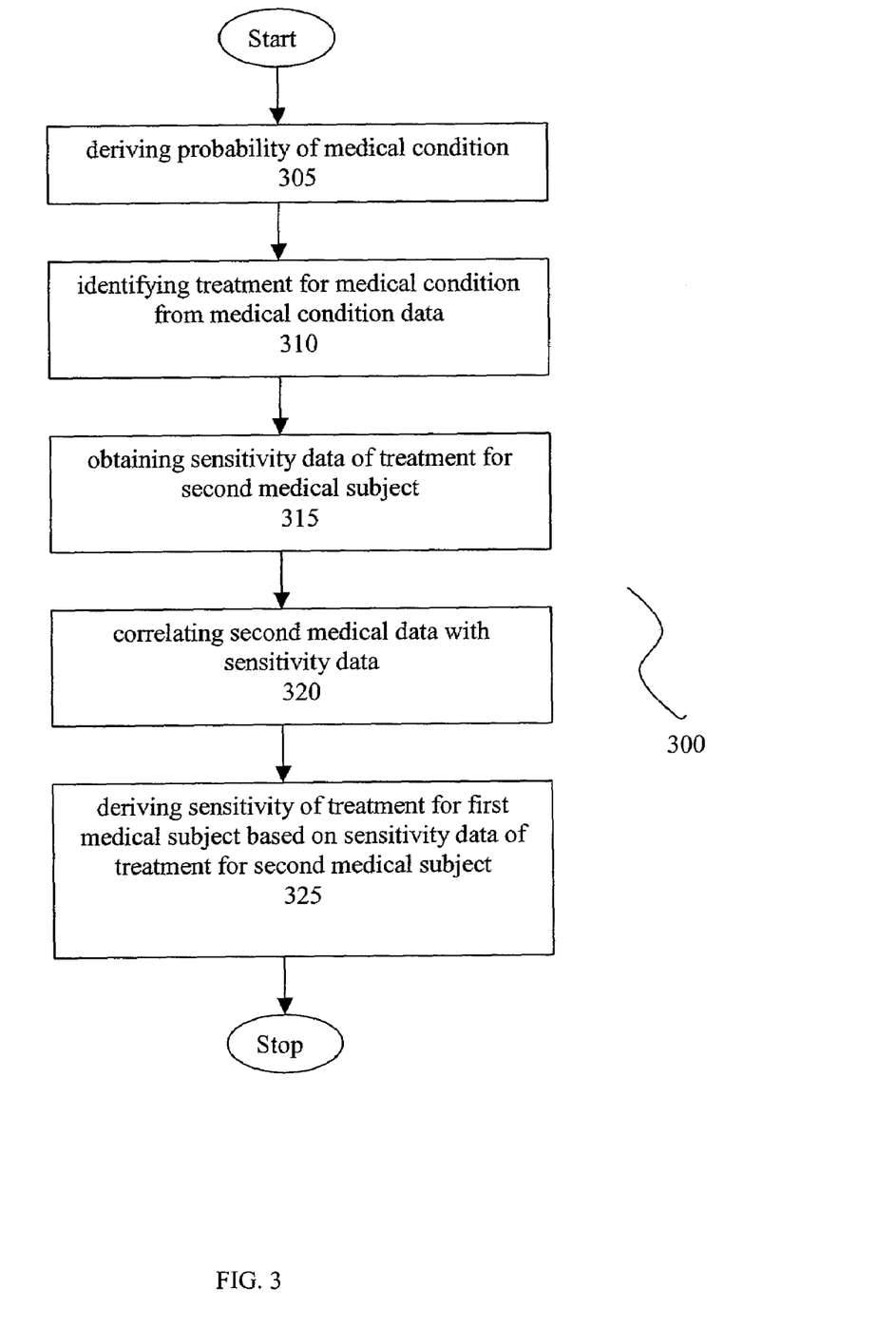
FIG. 3 shows a flow diagram of a method of predicting sensitivity of a treatment in a medical subject in an embodiment of the invention.
Figure 4:
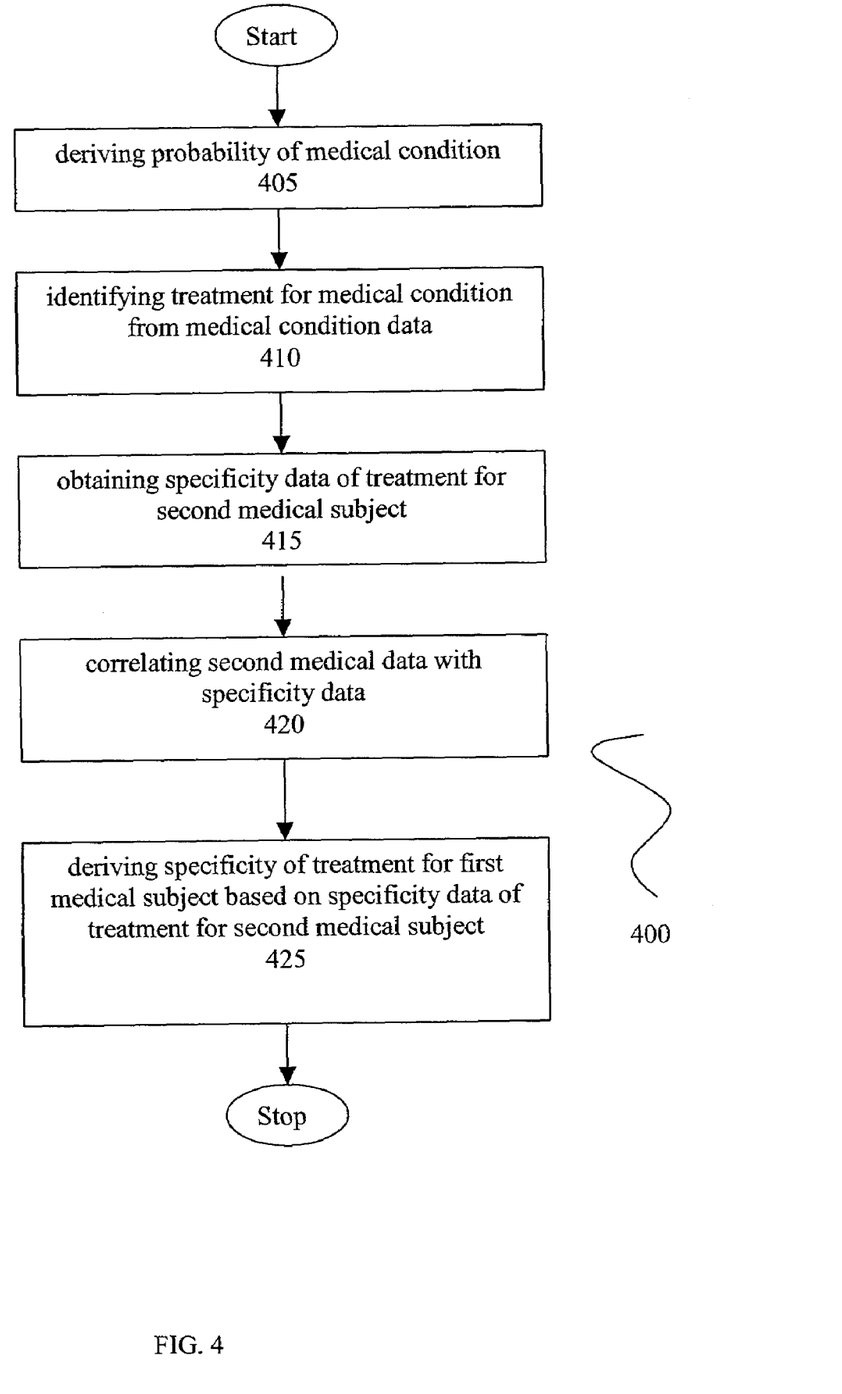
FIG. 4 shows a flow diagram of a method of predicting specificity of a treatment in a medical subject in an embodiment of the invention.

Furthermore, the medical condition data may include identification data of a treatment such as generic name of a medication, brand name of a medication, name of the manufacturer along with sensitivity data and specificity data corresponding to each treatment in a medical subject, which is further explained in conjunction with FIG. 3 and FIG. 4.

Through analysis of the first medical data and the medical condition data it may be possible to identify relationships within the data set and predict clinical outcome for a medical subject, when only the diagnostic and demographic data of the medical subject are known.

Further, multiple second medical data may be merged and/or correlated to create a family tree depicting a pattern of the medical condition. A probability index depicting the probability of the medical condition may also be identified along with the family tree.

Figure 2:
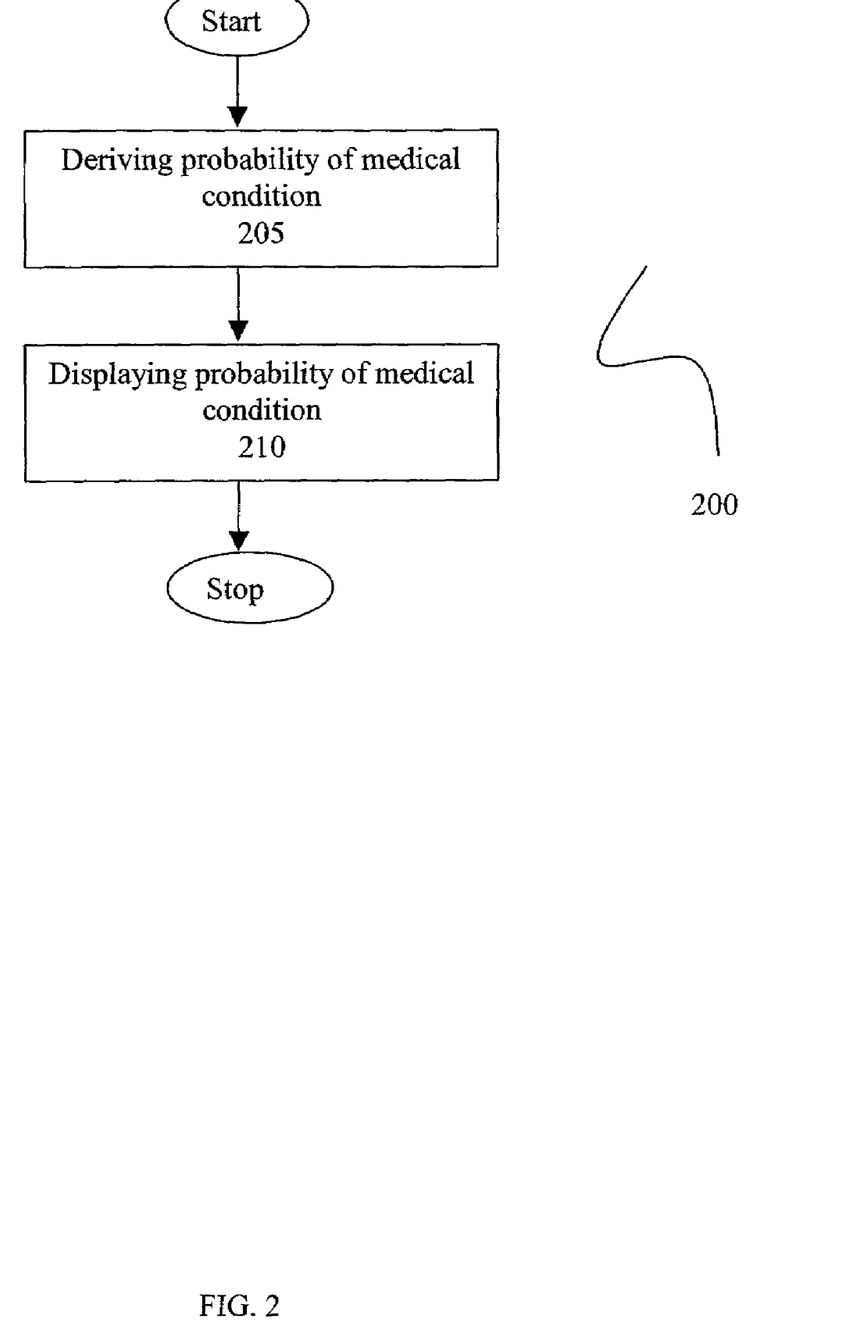
FIG. 2 shows a flow diagram of a method of predicting a medical condition in a medical subject in another embodiment of the invention.

FIG. 2 shows a flow diagram of a method 200 of predicting a medical condition in the first medical subject in another embodiment of the invention. The method 200 comprises predicting probability of the medical condition in the first medical subject step 205 and displaying probability of the medical condition step 210. The probability may be displayed via a user interface. This is further explained in conjunction with FIG. 5.

Upon predicting a medical condition in a medical subject as described in methods 100 and 200, the user can identify at least one treatment that can be used for treating the medical condition. The treatment may comprise administration of a medical procedure (therapeutic or surgical) and/or a drug or a derivative of the drug. As another non-limiting example, consider two medical subjects having similar demographics and medical condition characteristics, and wherein identical treatments are administered. One of the medical subjects responds to the treatment while the other does not. It is unclear why there are differences in reaction although each has the same medical condition. A desired solution is sought to predict which treatment is more beneficial for a particular medical subject.

Sensitivity and specificity are one approach to quantifying the therapeutic ability of a treatment. The response of a medical subject to the treatment, termed as sensitivity data or specificity data may be obtained in the form of percentage score appropriately indicating the response of a group of medical subjects to the treatment. In clinical practice, the sensitivity and specificity profile of the treatment provides information as to how good the treatment is at treating the medical condition. In other words, what proportions of medical subjects administered with the treatment are truly healed of the medical condition.

The sensitivity and specificity data so obtained may be used to form a statistical analysis, including predicting value of sensitivity and specificity of a given treatment in a medical subject.

FIG. 3 shows a flow diagram of a method 300 of predicting sensitivity of a treatment in the first medical subject in one embodiment of the invention. The method 300 comprises deriving probability of a medical condition step 305. The step 305 as described above comprises obtaining specific information with regard to the first medical subject, obtaining the first medical data of the first medical subject from a medical information system, obtaining the second medical data of the first medical subject from an electronic data system, identifying at least one second medical subject with a second medical data substantially same as the second medical data of the first medical subject, obtaining medical condition data for the second medical subject, correlating the first medical data with the medical condition data and deriving probability of the medical condition in the first medical subject based on the first medical data and the medical condition data.

The method 300 further comprises identifying a treatment for the medical condition in the first medical subject from the medical condition data step 310, obtaining sensitivity data for the treatment for the second medical subject step 315, analyzing the sensitivity data with respect to the second medical data step 320 and outputting sensitivity of treatment comprising information as to the likely response of the first medical subject to treatment protocols or suggested treatment options based on the analysis of the sensitivity data with respect to the relevant second medical data step 325.

FIG. 4 shows a flow diagram of a method 400 of predicting specificity of a treatment in the first medical subject in another embodiment of the invention. The method 400 comprises deriving probability of a medical condition step 405, identifying a treatment for the medical condition from the medical condition data step 410, obtaining specificity data of the treatment for the second medical subject step 415, analyzing the specificity data with respect to the second medical data step 420 and outputting specificity of the treatment comprising information as to the likely response of the first medical subject to treatment protocols or suggested treatment options based on the analysis of the specificity data with respect to the relevant second medical data step 425.

For example, if a given treatment protocol has been markedly beneficial with a given set of second medical subjects with the second medical data substantially same as that of the first medical subject, then such treatment protocol may be recommended for future medical subjects including the first medical subject that display the substantially same or similar set of second medical data.

The sensitivity and specificity data may be used by a medical staff such as a physician and/or a hospital administrator and/or a pharmaceutical company for generating information on the number of medical subjects with a medical condition, the sensitivity profile of a treatment to a medical condition and the specificity profile of a treatment to a medical condition.

Figure 5:
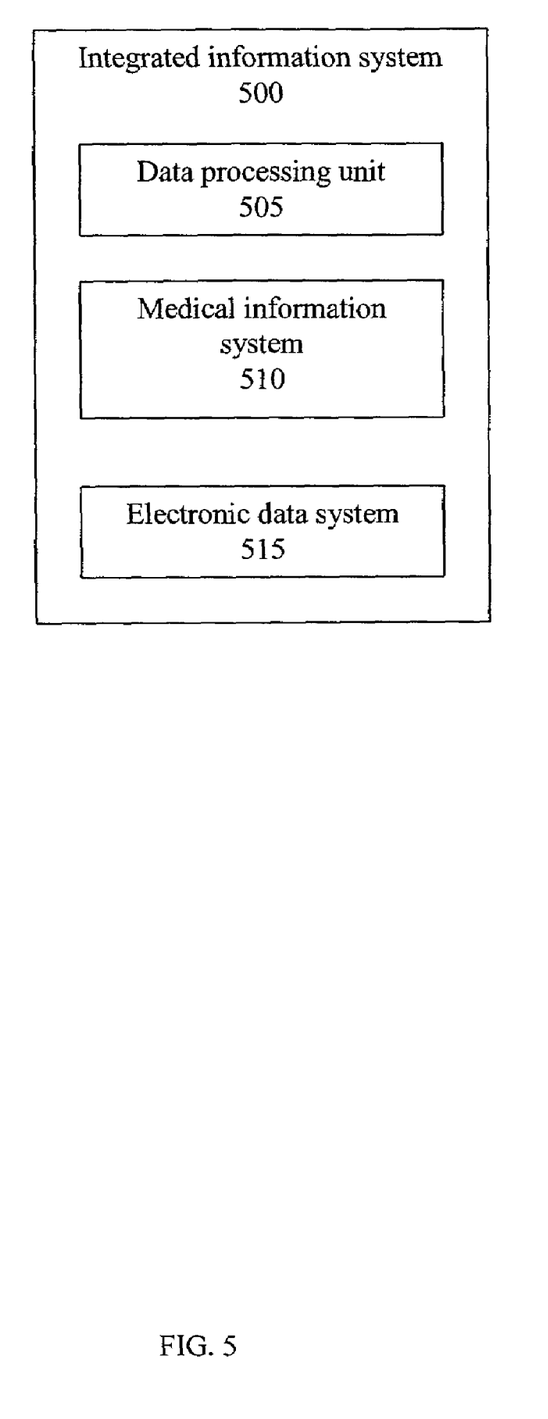
FIG. 5 shows a block diagram of an integrated information system in an embodiment of the invention.

In another embodiment, a system for performing the method 100 and 200 described above is provided. FIG. 5 shows a block diagram of an integrated information system 500 provided in one embodiment of the invention. The integrated information system 500 includes one or more medical information systems 510 for providing the first medical data of a medical subject, an electronic data system 515 for providing the second medical data of the medical subject and a data processing unit 505. The medical information system 510 and the electronic data systems 515 are communicatively coupled to the data processing unit 505.

The medical information system 510 comprises one of a picture archival and communication system (PACS), a laboratory information system (LIS), a hospital information system (HIS), a radiology information system (RIS) and a clinical information system (CIS). Skilled artisans shall however appreciate that the examples of the medical information systems 510 are not exclusive and the invention shall have full scope of the claims.

The plurality of medical information systems 510 may be connected to each other via a network. An example of the network is a Local Area Network (LAN), such as an Ethernet, installed in a healthcare organization such as a hospital or a medical facility. The LAN may also be connected to the Internet or another LAN in another hospital or medical facility via a dedicated line or a public telecommunication line such as ISDN. The network can be interconnected via a hard-wired connection (e.g., cable, bus, etc.) or a wireless connection (e.g., infrared, radio frequency, etc.) or combination thereof.

The electronic data system 515 comprises one or more databases. Each database may comprise a list of one or more medical subjects, the second medical data associated with each medical subject, a list of medical conditions observed in each medical subject and a list of medical condition data associated with each medical condition observed in each medical subject.

The data set comprising the list of medical subjects, the second medical data of the medical subjects, a list of medical conditions observed in each medical subject and a list of medical condition data may be derived from a variety of sources and from different data collection approaches. The data sources may include clients, consumers, sensors, medical devices, medical institutions, governmental agencies and a facilitation and creation of information sharing platform, whereby medical and other records are collected and uploaded to electronically accessible locations particularly databases. The data captured may include various historical, medical, environmental and other criteria and reports. The locations of the information entry might be connected through methods such as Internet connections, closed circuit connections, direct lines, cellular network, wide area networks, satellite and radio links.

In one embodiment, the electronic data system 515 can be a part of one of the medical information systems 510 such as CIS, RIS, LIS, HIS and PACS or can be a part of a separate medical workstation.

Figure 6:
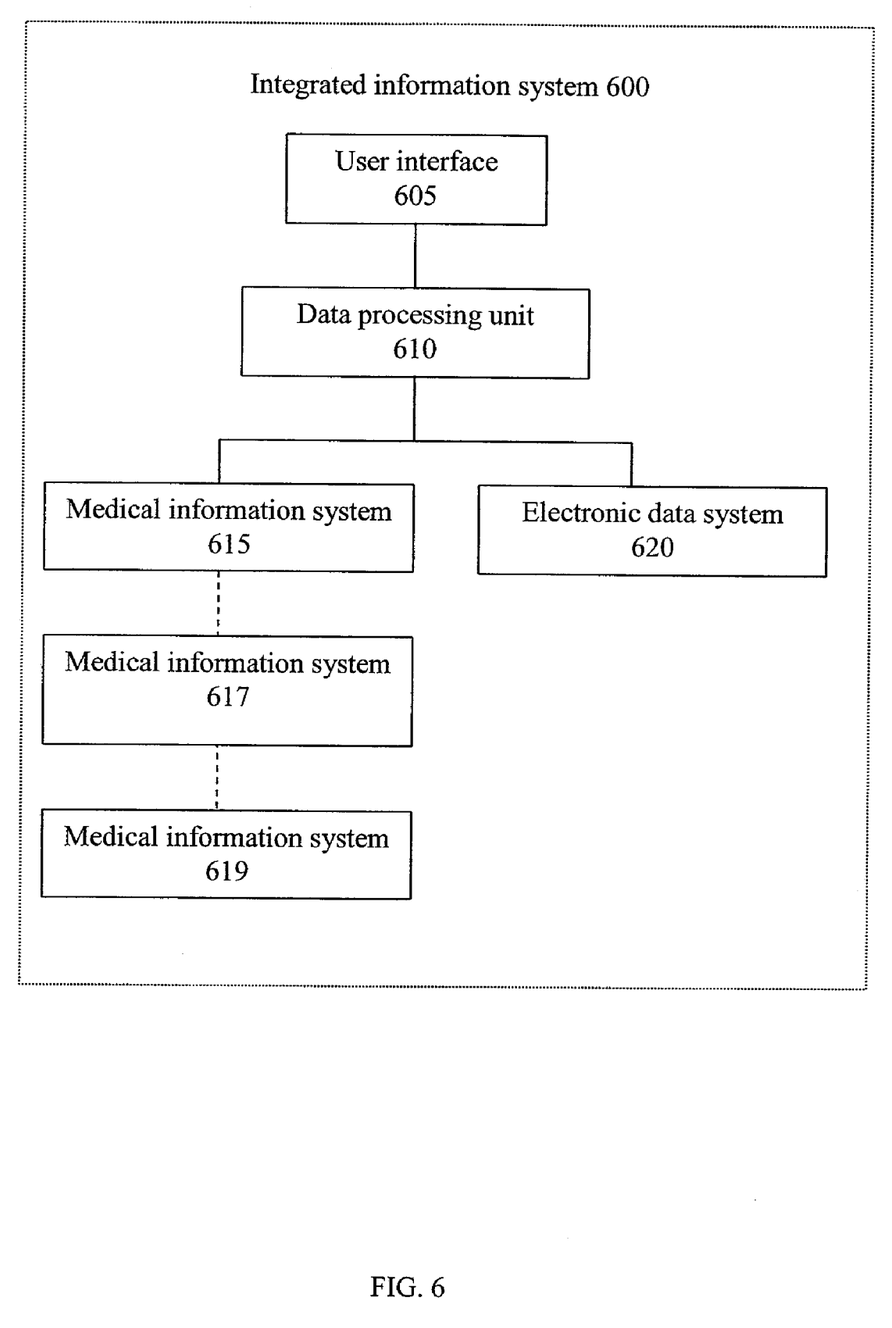
FIG. 6 shows a block diagram of an integrated information system in another embodiment of the invention.

FIG. 6 shows a block diagram of an integrated information system 600 provided in another embodiment. The integrated information system 600 comprises a user interface 605, a data processing unit 610, multiple medical information systems 615, 617 and 619 coupled to the data processing unit 610 and an electronic data system 620 coupled to the data processing unit 610.

The data processing unit 610 is configured for providing an outcome by analyzing the first medical data in the context of the second medical data and the medical condition data. The data processing unit 610 may include a data storage component, a data retrieval component, a data abstraction component and a data analysis component. Other components are also possible, and the interaction and sequence of function may vary between the components as long as they perform a substantially same function of diagnosing and/or predicting the occurrence of a medical condition based on the first medical data and the second medical data.

The data processing unit 610 is programmed to receive the first medical data from the medical information system 615, 617 and 619 and the second medical data from the electronic data system 620, identify at least one second medical subject with a second medical data substantially same as that of the first medical subject and retrieve medical condition data associated with the second medical subject, analyze the first medical data with respect to the medical condition data, and output information as to the probability of occurrence of the medical condition in the first medical subject and/or suggested treatment options for the medical condition based on the comparison of the first medical data to the medical condition data.

The data retrieval component can be configured to retrieve data from multiple medical information systems 615, 617 and 619 and the electronic data system 620. The data so obtained can be stored in the data storage component. The data abstraction component can be configured to integrate the data obtained from the medical information systems 615, 617 and 619 and the electronic data system 620. Thus, the function of the data abstraction component is to aggregate the first medical data, the second medical data and the medical condition data. The integrated data from the data abstraction component can be fed as an input to the data analysis component.

The data analysis component, which may be based on a neural network system, provides prediction of the occurrence of a medical condition in the first medical subject which may be an outcome based upon the first medical data of the first medical subject and the second medical data of a number of second medical subjects. The primary function of the data analysis component is to identify relationships within the database of medical subjects sharing the substantially same second medical data that can then be used to predict the probability of a medical condition and/or treatment options for the medical condition and/or treatment response. The data analysis component may comprise a rule-based module to provide outcome predictions, treatment recommendations, and/or clinical trial matching by using relationships gathered from the statistical analysis of the second medical data, medical condition data, standard medical protocols, and clinical trial databases.

The function of the data analysis unit uses sufficient second medical data and medical condition data within the electronic data system 620 so as to render predictive components statistically significant, and to accurately predict the outcome.

In an exemplary embodiment, a medical staff diagnosing a medical subject with a breast cancer may not be able to detect the presence of cancer by reading a mammography image. The integrated information system 600 provided in one embodiment of the invention is capable of providing context-based alerts and probability indexes based on the correlation between the first medical data i.e., the mammography image and the medical condition data of at least one second medical subject. The second medical subject can be a parent of the medical subject being diagnosed, both sharing a common second medical data i.e., the last name. If the parent of the medical subject had suffered a breast cancer, the possibility of the medical subject having the breast cancer is high. The probability of the occurrence of the breast cancer in the medical subject can be provided using the integrated information system 600. This can be extended further for different vectors to predict any probability for certain indexes.

The data processing unit 610 and the electronic data system 620 may use a document management system that utilizes XML format to store, process and display information in a form format. Such document management system makes use of clean XML (that is without any metadata) format on the database while manipulations of the data, which is done by a variety of software tools available, is being done on a copy. Prior to re-storing the form containing the processed information one or more metadata associated with the form is being separated from the form and saved separately from the form and is indexed and associated with the particular form. This document management system provides for modularity, versatility, scalability and enhanced functionality of the integrated information system 600 as many applications and interfaces may be used to process and display the information stored.

Further, the integrated information system 600 may be initiated and managed by a customer management system (CMS) that directs the flow of data and tracks the use and flow of data. The CMS serves as the administrative hub between a user (e.g. a clinician requesting analysis of a medical subject), and the integrated information system 600, both for the receipt of a request from the user and for the return of a report to the user. The report may take the form of an XML document. The XML document is then converted into the appropriate form, such as, for example, portable document format (PDF), postscript, rich text format (RTF), or others.

In an exemplary embodiment, the user inputs identification data of a medical subject into a web page. The identification data is sent to the integrated information system 600 where analysis is conducted. Result-ant data is produced and relayed back to the user, including for example, probability of occurrence of a medical condition, medical condition data information and statistics and potential treatment options along with predicted outcomes.

The integrated information system 600 substantially decreases the effort involved in gathering information from a number of medical subjects, performing the diagnosis and considering numerous treatment options before making a recommendation. Furthermore, because the resultant data provided to the user is based on a plurality of sensitivity data and specificity data of medical subjects with a second medical data substantially same as that of the first medical subject, the recommended course of treatment is based on proven data that best matches particular characteristics of the first medical subject.

As described above, each of the modules and components of the system 600 contributes an integral component to the overall functionality of the system 600. However, the system 600 and its methodology are not constrained by the type of technology employed to execute the function. Technology employed can be altered, substituted or eliminated without constraining the viability or function of the system 600.

The system 600 and method 100 provided in the invention for predicting a medical condition in a medical subject support a user's ability to carry out the diagnosis. The system and method provided in the invention are not intended to dictate to the user what the medical condition is or what the treatment is going to be, but to provide the user with medical subject-specific information to allow the user to make a decision on the diagnosis, treatment options and how best to treat the medical subject.

In another embodiment, a predictability engine for predicting the probability of occurrence of a medical condition is provided. The predictability engine is a computer program product stored in a computer readable media for predicting probability of a medical condition in a first medical subject. The computer program product comprises a routine for obtaining a first medical data corresponding to the first medical subject from at least one medical information system 615, 617 and 619, a routine for obtaining a second medical data corresponding to the first medical subject from the electronic data system 620, a routine for selecting at least one second medical subject with a second medical data based on the second medical data of the first medical subject, a routine for obtaining medical condition data for the second medical subject, a routine for correlating the first medical data with the medical condition data; and a routine for deriving probability of the medical condition in the first medical subject based upon the first medical data and the medical condition data. The computer program may further comprise a routine for displaying the probability of the medical condition via a user interface.

In another embodiment, the computer program product may further comprise a routine for identifying a treatment for the medical condition from the medical condition data and a routine for predicting sensitivity of the treatment in the first medical subject. The routine for predicting sensitivity of the treatment comprises a routine for obtaining sensitivity data of the treatment for the second medical subject, a routine for correlating the second medical data with the sensitivity data and a routine for deriving sensitivity of the treatment for the first medical subject based on the sensitivity data of the treatment for the second medical subject.

In yet another embodiment, the computer program product may further comprise a routine for predicting specificity of the treatment in the first medical subject. The routine for predicting specificity of the treatment comprises a routine for obtaining specificity data of the treatment for the second medical subject, a routine for correlating the second medical data with the specificity data and a routine for deriving specificity of the treatment for the first medical subject based on the specificity data of the treatment for the second medical subject.

A clinic or other health care institution may benefit greatly from use of the systems or methods provided in the invention. The greater use of technology will aid such organizations greatly in diagnosing and treating several medical conditions. Alternatively, such a tool may become standardized throughout the healthcare industry and be connectable through ubiquitous means, such as the Internet, and run off a remote server. Thus, as long as a health care worker has access to the Internet, such worker may have access to the integrated information system in diagnosing and treating a medical condition. Health care workers in remote areas, such as in isolated regions of the world without landlines, may still have access to the integrated information system through wireless connection devices, such as personal data assistants ("PDAs"), portable computers, or the like.

The invention enhances the accuracy, speed and cost effectiveness of diagnosing medical conditions and detecting environmental abnormalities. This is desired in particular, in situations where infectious medical conditions and chemical, biological or nuclear weapons are prevalent. The utilization of multiple sources driven information that is routinely captured and analyzed, the utilization of multiple data information systems connected via the network, and the ability to continuously refine and calibrate the system and generate real-time reporting and alerts, provides an essential advantage over fixed diagnostic tools, and/or over non-networked solutions.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of deriving probability of a medical condition, the method comprising:
    obtaining a first medical data corresponding to a first medical subject from at least one medical information system;
    obtaining a second medical data corresponding to the first medical subject from an electronic data system;
    selecting at least one second medical subject with a second medical data based on the second medical data of the first medical subject;
    obtaining medical condition data for the second medical subject, wherein the medical condition data comprises data corresponding to a medical condition;
    correlating the first medical data with the medical condition data; and
    deriving probability of the medical condition in the first medical subject based upon the first medical data and the medical condition data.

2. The method of claim 1, wherein the second medical data of the second medical subject is substantially same as the second medical data of the first medical subject.

3. The method of claim 1, further comprising displaying the probability of the medical condition via a user interface.

4. The method of claim 1, wherein the second medical data comprises at least one of last name of the first medical subject, ethnicity of the first medical subject, genetic data of the first medical subject and ancestral data of the first medical subject.

5. The method of claim 1, further comprising:
   identifying a treatment for the medical condition from the medical condition data;
   predicting sensitivity of the treatment in the first medical subject; and
   predicting specificity of the treatment in the first medical subject.

6. The method of claim 5, wherein predicting sensitivity of the treatment comprises:
   obtaining sensitivity data of the treatment for the second medical subject;
   correlating the second medical data with the sensitivity data; and
   deriving sensitivity of the treatment for the first medical subject based on the sensitivity data of the treatment for the second medical subject.

7. The method of claim 5, wherein predicting specificity of the treatment comprises:
   obtaining specificity data of the treatment for the second medical subject;
   correlating the second medical data with the specificity data; and
   deriving specificity of the treatment for the first medical subject based on the specificity data of the treatment for the second medical subject.

8. An integrated information system comprising:
   a data processing unit;
   at least one medical information system coupled to the data processing unit, wherein the medical information system is configured for providing a first medical data associated with a first medical subject; and
   an electronic data system coupled to the data processing unit, wherein the electronic data system is configured for providing a second medical data associated with the first medical subject;
   wherein the data processing unit is configured for selecting at least one second medical subject with a second medical data based on the second medical data of the first medical subject, obtaining medical condition data for the second medical subject, wherein the medical condition data comprises data corresponding to a medical condition, correlating the first medical data with the medical condition data, and deriving a probability of the medical condition in the first medical subject based on the first medical data and the medical condition data.

9. The integrated information system of claim 8, further comprising a user interface configured for displaying the probability of the medical condition.

10. The integrated information system of claim 8, wherein a plurality of medical information systems are connected via a network.

11. The integrated information system of claim 8, wherein the electronic data system comprises at least one database.

12. The integrated information system of claim 8, wherein the second medical data comprises at least one of last name of the first medical subject, ethnicity of the first medical subject, ancestral data of the first medical subject and genetic data of the first medical subject.

13. A computer program product stored in a computer readable media for predicting probability of a medical condition in a first medical subject, the computer program product comprising:
   a routine for obtaining a first medical data corresponding to the first medical subject from at least one medical information system;
   a routine for obtaining a second medical data corresponding to the first medical subject from an electronic data system;
   a routine for selecting at least one second medical subject with a second medical data based on the second medical data of the first medical subject;
   a routine for obtaining medical condition data for the second medical subject, wherein the medical condition data comprises data corresponding to a medical condition;
   a routine for correlating the first medical data with the medical condition data; and
   a routine for deriving probability of the medical condition in the first medical subject based upon the first medical data and the medical condition data.

14. The computer program product of claim 13, wherein the second medical data of the second medical subject is substantially same as the second medical data of the first medical subject.

15. The computer program product of claim 13, further comprising a routine for displaying the probability of the medical condition via a user interface.

16. The computer program product of claim 13, further comprising:
   a routine for identifying a treatment for the medical condition from the medical condition data;
   a routine for predicting sensitivity of the treatment in the first medical subject; and
   a routine for predicting specificity of the treatment in the first medical subject.

17. The computer program product of claim 16, wherein the routine for predicting sensitivity of the treatment comprises:
   a routine for obtaining sensitivity data of the treatment for the second medical subject;
   a routine for correlating the second medical data with the sensitivity data; and
   a routine for deriving sensitivity of the treatment for the first medical subject based on the sensitivity data of the treatment for the second medical subject.

18. The computer program product of claim 16, wherein the routine for predicting specificity of the treatment comprises:
   a routine for obtaining specificity data of the treatment for the second medical subject;
   a routine for correlating the second medical data with the specificity data; and
   a routine for deriving specificity of the treatment for the first medical subject based on the specificity data of the treatment for the second medical subject.

* * * * *